US011167123B2

(12) United States Patent
Agarwal et al.

(10) Patent No.: US 11,167,123 B2
(45) Date of Patent: Nov. 9, 2021

(54) COORDINATED VENTRICULAR ASSIST AND CARDIAC RHYTHM MANAGEMENT DEVICES AND METHODS

(71) Applicant: TC1 LLC, St. Paul, MN (US)

(72) Inventors: Rahul Agarwal, Los Angeles, CA (US); Allison Connolly, Fremont, CA (US); Yelena Nabutovsky, Mountain View, CA (US); Julie Prillinger, Redwood City, CA (US)

(73) Assignee: TC1 LLC, St. Paul, MN (US)

( * ) Notice: Subject to any disclaimer, the term of this patent is extended or adjusted under 35 U.S.C. 154(b) by 229 days.

(21) Appl. No.: 16/295,375

(22) Filed: Mar. 7, 2019

(65) Prior Publication Data

US 2019/0282745 A1 Sep. 19, 2019

Related U.S. Application Data

(60) Provisional application No. 62/644,858, filed on Mar. 19, 2018.

(51) Int. Cl.
*A61M 60/00* (2021.01)
*A61M 60/148* (2021.01)
(Continued)

(52) U.S. Cl.
CPC ........... *A61M 60/148* (2021.01); *A61B 5/024* (2013.01); *A61M 60/50* (2021.01); *A61N 1/362* (2013.01);
(Continued)

(58) Field of Classification Search
None
See application file for complete search history.

(56) References Cited

U.S. PATENT DOCUMENTS 3,911,897 A 10/1975 Leachman
5,020,544 A * 6/1991 Dahl .................... A61N 1/0587
607/129
(Continued)

FOREIGN PATENT DOCUMENTS

EP 2 570 143 A1 3/2013
EP 3 213 781 A1 9/2017
(Continued)

OTHER PUBLICATIONS

Bedi et al., "Ventricular Arrhythmias During Left Ventricular Assist Device Support", Am J Cardiol., vol. 99, Issue 8, 2007, pp. 1151-1153.

(Continued)

*Primary Examiner* — John R Downey
*Assistant Examiner* — Anant A Gupta
(74) *Attorney, Agent, or Firm* — Kilpatrick Townsend & Stockton LLP

(57) ABSTRACT

Controllers and methods for heart treatments are disclosed herein. The controller can include a communication module that can send and receive data from heart therapy devices. The controller can include memory including stored instruction. The controller can include a processor. The processor can receive a signal of an impending electrical treatment at a processor. The processor can determine a current operating parameter of a blood pump communicatingly coupled with the processor. The processor can determine an adjustment to the operating parameter of the blood pump to affect an impedance of heart tissue to be affected by the impending electrical treatment. The processor can control the blood pump according to the adjustment to the operating parameter of the blood pump.

30 Claims, 7 Drawing Sheets

(51) Int. Cl.
  *A61N 1/362* (2006.01)
  *A61N 1/372* (2006.01)
  *A61B 5/024* (2006.01)
  *A61N 1/365* (2006.01)
  *A61M 60/50* (2021.01)
  *A61N 1/39* (2006.01)
  *A61B 5/363* (2021.01)
  *A61M 60/871* (2021.01)

(52) U.S. Cl.
  CPC ....... *A61N 1/3627* (2013.01); *A61N 1/36521* (2013.01); *A61N 1/372* (2013.01); *A61N 1/37252* (2013.01); *A61B 5/363* (2021.01); *A61M 60/871* (2021.01); *A61M 2210/125* (2013.01); *A61N 1/3962* (2013.01)

(56) References Cited

U.S. PATENT DOCUMENTS

| | | |
|---|---|---|
| 5,139,517 A | 8/1992 | Corral |
| 5,318,592 A | 6/1994 | Schaldach |
| 5,503,615 A | 4/1996 | Goldstein |
| 6,066,086 A | 5/2000 | Antaki et al. |
| 6,111,520 A | 8/2000 | Allen et al. |
| 6,278,379 B1 | 8/2001 | Allen et al. |
| 6,585,635 B1 | 7/2003 | Aldrich |
| 6,634,224 B1 | 10/2003 | Schoeb et al. |
| 6,643,420 B2 | 11/2003 | Han et al. |
| 6,772,011 B2 | 8/2004 | Dolgin et al. |
| 6,855,115 B2 | 2/2005 | Fonseca et al. |
| 6,984,201 B2 | 1/2006 | Khaghani et al. |
| 7,029,433 B2 | 4/2006 | Chang |
| 7,245,117 B1 | 7/2007 | Joy et al. |
| 7,320,706 B2 | 1/2008 | Al-Najjar |
| 7,439,723 B2 | 10/2008 | Allen et al. |
| 7,498,799 B2 | 3/2009 | Allen et al. |
| 7,520,850 B2 | 4/2009 | Brockway |
| 7,550,978 B2 | 6/2009 | Joy et al. |
| 7,679,355 B2 | 3/2010 | Allen et al. |
| 7,839,153 B2 | 11/2010 | Joy et al. |
| 7,853,325 B2 | 12/2010 | Dabney et al. |
| 7,862,501 B2 | 1/2011 | Woodard |
| 7,945,333 B2 | 5/2011 | Jacobson |
| 7,963,905 B2 | 6/2011 | Salmonsen et al. |
| 7,988,728 B2 | 8/2011 | Ayre |
| 7,998,054 B2 | 8/2011 | Bolling |
| 8,145,324 B1 | 3/2012 | Stevenson et al. |
| 8,177,838 B2 | 5/2012 | Vodermayer et al. |
| 8,180,448 B2 | 5/2012 | Stevenson et al. |
| 8,224,462 B2 | 7/2012 | Westlund et al. |
| 8,246,530 B2 | 8/2012 | Sullivan |
| 8,295,939 B2 | 10/2012 | Jacobson |
| 8,364,283 B2 | 1/2013 | Halperin et al. |
| 8,506,471 B2 | 8/2013 | Bourque |
| 8,543,205 B2 | 9/2013 | Ostroff |
| 8,608,636 B2 | 12/2013 | Choi et al. |
| 8,657,733 B2 | 2/2014 | Ayre et al. |
| 8,682,431 B2 | 3/2014 | Callaway et al. |
| 8,712,544 B2 | 4/2014 | Dabney et al. |
| 8,771,165 B2 | 7/2014 | Choi et al. |
| 8,794,989 B2 | 8/2014 | Kearsley et al. |
| 8,852,099 B2 | 10/2014 | Von Arx et al. |
| 8,864,644 B2 | 10/2014 | Yomtov |
| 8,894,561 B2 | 11/2014 | Callaway et al. |
| 8,897,887 B2 | 11/2014 | Halperin et al. |
| 9,039,595 B2 | 5/2015 | Ayre et al. |
| 9,090,271 B2 | 7/2015 | Bartonek |
| 9,387,284 B2 | 7/2016 | Heilman et al. |
| 9,433,714 B2 | 9/2016 | Voskoboynikov et al. |
| 9,579,432 B2 | 2/2017 | Tamez et al. |
| 9,579,435 B2 | 2/2017 | Yomtov |
| 9,592,327 B2 | 3/2017 | Wariar et al. |
| 9,833,552 B2 | 12/2017 | Yomtov |
| 2005/0071001 A1 | 3/2005 | Jarvik |
| 2007/0088397 A1 | 4/2007 | Jacobson |
| 2007/0265703 A1* | 11/2007 | Sutton ................. A61M 1/1086 623/3.1 |
| 2007/0276300 A1* | 11/2007 | Olson ................. A61H 31/007 601/41 |
| 2008/0281146 A1 | 11/2008 | Morello |
| 2009/0043241 A1* | 2/2009 | Pecor ................. A61M 39/1011 604/6.16 |
| 2009/0264945 A1* | 10/2009 | Doerr ..................... A61N 1/371 607/4 |
| 2010/0241223 A1 | 9/2010 | Lee et al. |
| 2011/0077574 A1* | 3/2011 | Sigg ................. A61M 1/3403 604/6.01 |
| 2011/0178361 A1 | 7/2011 | Yomtov |
| 2011/0270331 A1 | 11/2011 | Peters et al. |
| 2013/0066142 A1* | 3/2013 | Doerr ................. A61M 60/148 600/17 |
| 2013/0072846 A1 | 3/2013 | Heide et al. |
| 2014/0012067 A1 | 1/2014 | Poirier |
| 2014/0046120 A1 | 2/2014 | Choi et al. |
| 2014/0058190 A1 | 2/2014 | Gohean et al. |
| 2014/0188148 A1 | 7/2014 | Le Blanc et al. |
| 2015/0057488 A1 | 2/2015 | Yomtov |
| 2015/0073203 A1 | 3/2015 | Wariar et al. |
| 2015/0141911 A1* | 5/2015 | Bulent ................. A61M 1/3607 604/66 |
| 2015/0148587 A1 | 5/2015 | Bourque |
| 2015/0151032 A1 | 6/2015 | Voskoboynikov et al. |
| 2015/0174307 A1 | 6/2015 | Eckman et al. |
| 2015/0290374 A1 | 10/2015 | Bourque et al. |
| 2015/0290375 A1* | 10/2015 | Angwin ................. A61M 1/122 600/17 |
| 2015/0328466 A1 | 11/2015 | Peters et al. |
| 2016/0058929 A1 | 3/2016 | Medvedev et al. |
| 2016/0058930 A1 | 3/2016 | Medvedev et al. |
| 2016/0101230 A1 | 4/2016 | Ochsner et al. |
| 2016/0193397 A9 | 7/2016 | Aber et al. |
| 2016/0228628 A1 | 8/2016 | Medvedev et al. |
| 2016/0263299 A1 | 9/2016 | Xu et al. |
| 2017/0021070 A1 | 1/2017 | Petersen |
| 2017/0080138 A1 | 3/2017 | Yomtov |
| 2018/0050348 A1 | 2/2018 | Whitney |
| 2018/0078689 A1 | 3/2018 | Yomtov |
| 2018/0140760 A1 | 5/2018 | Cotter |
| 2018/0280599 A1 | 10/2018 | Harjes et al. |
| 2018/0280600 A1 | 10/2018 | Harjes et al. |
| 2018/0280601 A1 | 10/2018 | Harjes et al. |

FOREIGN PATENT DOCUMENTS

| | | |
|---|---|---|
| WO | 2007089500 A2 | 8/2007 |
| WO | 2011123789 A1 | 10/2011 |
| WO | 2016001284 A2 | 1/2016 |
| WO | 2016137743 A1 | 9/2016 |
| WO | 2017117185 A1 | 7/2017 |
| WO | 2017117215 A1 | 7/2017 |
| WO | 2017139113 A1 | 8/2017 |

OTHER PUBLICATIONS

Brisco et al., "The Incidence, Risk, and Consequences of Atrial Arrhythmias in Patients With Continuous-flow Left Ventricular Assist Devices", J Card Surg, vol. 29, Issue 4, 2014, pp. 572-580.
Clark et al., "Hemodynamic Effects of an Irregular Sequence of Ventricular Cycle Lengths During Atrial Fibrillation", Journal of the American College of Cardiology, vol. 30, Issue 4, 2007, pp. 1039-1045.
Enriquez et al., "Clinical Impact of Atrial Fibrillation in Patients With the Heartmate li Left Ventricular Assist Device", Journal of the American College of Cardiology, vol. 64, Issue 18, 2014, pp. 1883-1890.
Hayward et al., "Effect of Alteration in Pump Speed on Pump Output and Left Ventricular Filling With Continuous-flow Left Ventricular Assist Device", ASAIO Journal. vol. 57, issue 6, 2011, pp. 495-500.
Maeda et al., "Predictive Control by Physical Activity Rate of a Total Artificial Heart During Exercise", Transactions of the American Society of Artificial Internal Organs, vol. 34, 1988, pp. 480-484.

(56) References Cited

OTHER PUBLICATIONS

Maury et al., "First Experience of Percutaneous Radio-frequency Ablation for Atrial Flutter and Atrial Fibrillation in a Patient With Heartmate li Left Ventricular Assist Device", Journal of Interventional Cardiac Electrophysiology, vol. 29, Issue 1, 2010, pp. 63-67.

Oswald et al., "Implantable Defibrillator Therapy for Ventricular Tachyarrhythmia in Left Ventricular Assist Device Patients", Eur J Heart Fail., vol. 12, Issue 6, 2010, pp. 593-599.

Oz et al., "Malignant Ventricular Arrhythmias Are Well Tolerated in Patients Receiving Long-term Left Ventricular Assist Devices", Journal of the American College of Cardiology, vol. 24, Issue 7, 1994, pp. 1688-1691.

Raasch et al., "Epidemiology, Management, and Outcomes of Sustained Ventricular Arrhythmias After Continuous-flow Left Ventricular Assist Device Implantation", Am Heart J., vol. 164, Issue 3, 2012, pp. 373-378.

Ziv et al., "Effects of Left Ventricular Assist Device Therapy on Ventricular Arrhythmias", Journal of the American College of Cardiology, vol. 45, Issue 9, 2005, pp. 1428-1434.

\* cited by examiner

| Arrhythmia Type | Ventricular Rate | Arrhythmia Duration | Post-Implant Phase | VAD Action |
|---|---|---|---|---|
| Atrial Fibrillation | Fast (>100 bpm) | <7 days | Acute | Increment 4 |
| Atrial Fibrillation | Fast (>100 bpm) | ≥7 days | Acute | Increment 6 |
| Atrial Fibrillation | Fast (>100 bpm) | <7 days | Chronic | Increment 1 |
| Atrial Fibrillation | Fast (>100 bpm) | ≥7 days | Chronic | Increment 5 |
| Atrial Fibrillation | Slow (<100 bpm) | <7 days | Acute | No change |
| Atrial Fibrillation | Slow (<100 bpm) | ≥7 days | Acute | Increment 3 |
| Atrial Fibrillation | Slow (<100 bpm) | <7 days | Chronic | No change |
| Atrial Fibrillation | Slow (<100 bpm) | ≥7 days | Chronic | Increment 2 |
| PVC | - | >1 PVC | In response to VAD increase | Decrement |
| VT | Slow | - | In response to VAD increase | Decrement |
| VT | Fast | - | In response to VAD increase | Decrement |
| VT | Slow | >X intervals | Acute | Increment 3 |
| VT | Fast | >X intervals | Acute | Increment 5 |
| VT | Slow | >X intervals | Chronic | Increment 2 |
| VT | Fast | >X intervals | Chronic | Increment 4 |
| VF | - | >X intervals | Acute | Increment 6 |
| VF | - | >X intervals | Chronic | Increment 6 |

FIG. 7

COORDINATED VENTRICULAR ASSIST AND CARDIAC RHYTHM MANAGEMENT DEVICES AND METHODS

CROSS REFERENCE TO RELATED APPLICATIONS

The present application claims the benefit under 35 USC § 119(e) of U.S. Provisional Appln. No. 62/644,858 filed Mar. 19, 2018; the full disclosure which is incorporated herein by reference in its entirety for all purposes.

BACKGROUND

The present invention generally relates to heart failure and disease state management systems, and in various respects, methods and systems for communicating information between an implantable blood pump and another device like a cardiac rhythm management device.

Cardiovascular disease remains the leading cause of death globally. Nearly one third of deaths in the U.S. are caused by heart disease, stroke, and other cardiovascular diseases according to the American Heart Association. Nearly one in ten deaths have cardiovascular disease as a contributing factor. Because of the size of this epidemic—nearly 6 million adults in the United States live with heart failure—there remains a need for improving the early diagnosis and treatment of cardiovascular disease. Many people unknowingly live with heart disease until they experience a significant event.

More recently, Ventricular Assist Devices (VADs) have become increasingly common for treating advanced heart failure. Advanced heart failure patients usually refers to patients in New York Heart Association (NYHA) Class III or IV. VAD therapy patients often have several comorbidities such as renal failure, respiratory failure, and other cardiovascular diseases. VAD patients often have other cardiac treatment devices including implanted pacemakers (IPM), implantable cardioverter defibrillators (ICD), cardiac resynchronization therapy (CRT) devices, monitoring systems (e.g. CardioMEMS, implantable cardiac monitors, etc.), and/or other heart failure management devices. While VADs and cardiac implantable rhythm management (CIED) devices separately provide beneficial heart assist functions, it may be advantageous to communicate information between the implanted devices to diagnose disease, improve therapy through device coordination, and more. And because these systems are not designed to interoperate at present, there is a need for systems and methods to establish communication and interoperability.

There is a need for improved systems for diagnosing and treating heart disease. There is a need for systems and methods for coordinating mechanical assist devices and cardiac rhythm management devices.

BRIEF SUMMARY

The present invention generally relates to heart assist systems and treatments. In some embodiments, one or several operational parameters of a blood pump can be affected to mitigate an adverse heart condition and/or to create a better environment for delivery of electroshock therapy. This can include changing one or several operational parameters of the blood pump to increase and/or decrease blood flow through the blood pump. The determination to change one or several operational parameters of the blood pump can be based on information received indicative of heart performance such as, for example, the presence of one or several arrhythmias, a change in heart rate, or the like. Based on this received information, a change in one or several operational parameters of the blood pump can be determined, and the operation of the blood pump can be affected according to these changed one or several operational parameters.

In some embodiments, one or several operational parameters of the blood pump can be changed based on a detected condition of a patient's heart that is fluidly connected with the blood pump. These detected conditions can include, for example, one or several detected arrhythmias. In some embodiments, based on the detected condition and/or the severity of the detected condition, an adjustment to the operational parameter can be identified and/or retrieved and can be used to adjust the operational parameter of the blood pump such as, for example, to adjust the speed of the blood pump.

In some embodiments, the adjustment of the operational parameter of the blood pump can be further based on, for example, a temporal status. The temporal status can be indicative of an amount of time elapsed since implantation of the blood pump. In some embodiments, for example, likelihood of arrhythmia and/or adverse consequences of arrhythmia can be highest in a period immediately following implantation of the blood pump. In such embodiments, the adjustment may differ based on a determined temporal status.

One aspect of the present disclosure relates to a method of increasing battery life of an implantable cardiac rhythm management device. The method includes: receiving a signal of an impending electrical treatment at a processor; determining a current operating parameter of a blood pump operably coupled with the processor; determining an adjustment to the operating parameter of the blood pump to affect an impedance of a heart tissue to be affected by the impending electrical treatment; and controlling the blood pump for a first period of time based on at least the determined adjustment to affect the impedance of the heart tissue to be affected by the impending electrical treatment.

In some embodiments, the signal of the impending electrical treatment is received by a controller of the blood pump. In some embodiments, the current operating parameter of the blood pump can be at least one of: a pump speed; or a pumping operation mode. In some embodiments, the pumping operation mode can include at least one of: continuous pumping; or pulsatile pumping. In some embodiments, determining the adjustment to the operating parameter of the blood pump includes determining to at least one of: increase the pump speed; decrease the pump speed; or change the pumping operation mode to one of: continuous pumping; or pulsatile pumping. In some embodiments, the adjustment is determined based on at least one heart property, and in some embodiments, controlling the blood pump based on at least the determined adjustment to the operating parameter of the blood pump reduces the impedance of the heart tissue to be affected by the impending electrical treatment.

In some embodiments, the blood pump is controlled based on at least the determined adjustment to the operating parameter of the blood pump until at least a desired impedance range is determined. In some embodiments, an amount of energy required to effectively deliver the impending electrical treatment is reduced based on the reduced impedance of the heart tissue to be affected by the impending electrical treatment.

In some embodiments, the method includes reverting to the unadjusted operating parameter. In some embodiments, the method includes determining delivery of the electrical treatment prior to reverting to the unadjusted operating parameter. In some embodiments, determining delivery of the electrical treatment includes at least one of: receiving a signal of completion of electrical treatment; or detecting delivery of the electrical treatment. In some embodiments, detecting delivery of the electrical treatment can include at least one of: sensing an electrical attribute indicative of delivery of the electrical treatment; or sensing a vibration or conduction indicative of delivery of the electrical treatment. In some embodiments, the method includes waiting a predetermined time after receipt of the signal of the impending electrical treatment before reverting to the unadjusted operating parameter.

In some embodiments, the signal of an impending electrical treatment can be received at the processor from a cardiac rhythm management device. The cardiac rhythm management device can: determine to deliver the electrical treatment; transmit the signal of the impending electrical treatment; wait a predetermined time after transmitting the signal of the impending electrical treatment; and deliver the electrical treatment subsequent to waiting the predetermined time. In some embodiments, the impending electrical treatment is delivered after the impedance of the heart tissue is substantially affected according to the determined adjustment, based on an output signal transmitted from the heart pump, or after a second period of time. In some embodiments, the method can include receiving an additional signal of an additional impending electrical treatment when the delivered electrical treatment is determined as ineffective.

In some embodiments, the method can include receiving a signal of completion of electrical treatment when the delivered electrical treatment is determined as effective. In some embodiments, the electrical treatment can include at least one of: electroshock defibrillation; or electrical impulses. In some embodiments, the signal of the impending electrical treatment can be received via a wire coupled to the cardiac rhythm management device and at least one of: the blood pump and the processor. In some embodiments, the signal of the impending electrical treatment can be received via a wireless communication. In some embodiments, the signal of the impending electrical treatment can be wirelessly received via Bluetooth.

In some embodiments, the method can include: determining to deliver the electrical treatment; transmitting the signal of the impending electrical treatment; waiting a predetermined time after transmitting the signal of the impending electrical treatment; and delivering the electrical treatment subsequent to waiting the predetermined time. In some embodiments, the impending electrical treatment is delivered after the impedance of the heart tissue is substantially affected according to the determined adjustment, based on an output signal transmitted from the heart pump, or after a second period of time. In some embodiments, the method includes: determining an effectiveness of the delivered electrical treatment; and transmitting an additional signal of an additional impending electrical treatment when the delivered electrical treatment is ineffective.

In some embodiments, the method includes: determining an effectiveness of the delivered electrical treatment; and transmitting a signal of completion of electrical treatment when the delivered electrical treatment is effective. In some embodiments, the electrical treatment can include at least one of: electroshock defibrillation; or electrical impulses. In some embodiments, the signal of the impending electrical treatment is transmitted via a wire coupled to the cardiac rhythm management device and at least one of: the blood pump and the processor. In some embodiments, the signal of the impending electrical treatment is wirelessly transmitted. In some embodiments, the signal of the impending electrical treatment is wirelessly transmitted via Bluetooth.

In some embodiments, the cardiac rhythm management device includes at least one of: a cardioverter defibrillator, a cardiac resynchronization therapy device, or a pacemaker. In some embodiments, the blood pump comprises a ventricular assist device.

One aspect of the present disclosure relates to a heart blood pump controller. The heart blood pump controller includes: a communication module that can transmit and receive data from a cardiac rhythm management device; a memory containing stored instructions; and a processor. In some embodiments, the processor can: receive a signal of an impending electrical treatment; determine a current operating parameter of a heart blood pump operably coupled with the processor; determine an adjustment to the operating parameter of the blood pump to affect an impedance of a heart tissue to be affected by the impending electrical treatment; and control the blood pump according to the adjustment to the operating parameter of the blood pump.

In some embodiments, the signal of the impending electrical treatment is received from the cardiac rhythm management device communicatively coupled with the heart blood pump controller. In some embodiments, the current operating parameter of the blood pump can be at least one of: a pump speed; or a pumping operation mode. In some embodiments, determining the adjustment to the operating parameter of the blood pump can include determining to at least one of: an increase of the pump speed; a decrease in the pump speed; or a change in the pumping operation mode. In some embodiments, the pumping operation mode includes at least one of: continuous pumping; or pulsatile pumping.

In some embodiments, the processor can determine delivery of the electrical treatment. In some embodiments, determining delivery of the electrical treatment includes at least one of: receiving a signal of completion of electrical treatment; detecting delivery of the electrical treatment; and waiting a first predetermined time after receipt of the signal of the impending electrical treatment. In some embodiments, the processor can revert to the unadjusted operating parameter.

In some embodiments, detecting delivery of the electrical treatment includes at least one of: sensing an electrical attribute indicative of delivery of the electrical treatment; and sensing a vibration indicative of delivery of the electrical treatment. In some embodiments, the blood pump is controlled for a first period of time based on at least the determined adjustment to affect the impedance of the heart tissue to be affected by the impending electrical treatment. In some embodiments, the processor can adjust the operating parameter of the blood pump until a desired impedance is determined. In some embodiments, the controller is at least one of: an external controller; or an implantable controller. In some embodiments, the implantable controller is integral with the blood pump, and in some embodiments, the implantable controller is separate from the blood pump.

One aspect of the present disclosure relates to a method of delivering circulatory support to a patient with a heart blood pump. The method includes: receiving a signal with a heart blood pump controller of an arrhythmia; determining a categorization of the arrhythmia of the heart with the pump controller based on the received signal of the arrhythmia; identifying with the pump controller an adjustment to an operating parameter of a blood pump based on the determined categorization of the arrhythmia; and controlling the blood pump according to the adjusted operating parameter.

In some embodiments, the method includes determining a temporal status. In some embodiments, the adjustment to the operating parameter is identified based on the temporal status and on the categorization of the arrhythmia. In some embodiments, the temporal status is indicative of an amount of time elapsed since implantation of the blood pump. In some embodiments, a magnitude of the adjustment to the operating parameter of the blood pump decreases as the amount of time elapsed since implantation of the blood pump increases.

In some embodiments, the categorization of the arrhythmia identifies an arrhythmia type or an arrhythmia severity. In some embodiments, the arrhythmia type can include at least one of: an atrial fibrillation; premature ventricular contractions; ventricular fibrillation; and ventricular tachycardia. In some embodiments, the arrhythmia severity is determined based on at least one of: a duration of the arrhythmia; a ventricular rate; and one or several ventricular/supraventricular tachycardia discriminator values. In some embodiments, these one or several ventricular/supraventricular tachycardia discriminator values can include, for example, morphology of the electrical signal, regularity of the arrhythmia, suddenness of the arrhythmia onset, or the like.

In some embodiments, the adjustment to the operating parameter of the blood pump includes at least one of: incrementing a speed of the blood pump; and decrementing the speed of the blood pump. In some embodiments, the adjustment to the operating parameter of the blood pump includes changing a pumping operation mode. In some embodiments, the pumping operation mode includes at least one of: pulsatile pumping; or continuous pumping. In some embodiments, the method includes: determining a current operating parameter of the blood pump; retrieving a threshold value based on the current operating parameter; and comparing a speed of the blood pump operating at the adjusted operating parameter to the threshold value. In some embodiments, the threshold value delineates between acceptable speeds of the blood pump and unacceptable speeds of the blood pump.

In some embodiments, the method includes controlling the blood pump to operate at the speed corresponding to the threshold value, which threshold value can correspond to a maximum or minimum allowable pump speed, when the speed of the blood pump operating at the adjusted operating parameter exceeds the threshold value. In some embodiments, the signal is transmitted by an implantable cardiac electronic device via at least one of: a wired connection; a wireless connection; or conduction. In some embodiments, the implantable cardiac electronic device includes a cardioverter defibrillator, cardiac resynchronization therapy device, pacemaker, or sensor.

One aspect of the present disclosure relates to a heart blood pump controller. The heart blood pump controller includes: a communication module that can transmit and receive data from an implantable cardiac electronic device; a memory including a lookup table identifying a plurality of categories of arrhythmias and associated operating parameter adjustments; and a processor. In some embodiments, the processor can: receive a signal of an arrhythmia of a heart of a patient; categorize the arrhythmia of the heart based on the received signal of the arrhythmia; identify an adjustment to an operating parameter of a blood pump based on the categorization of the arrhythmia; and control the blood pump according to the adjusted operating parameter.

In some embodiments, the processor can determine a temporal status. In some embodiments, the adjustment to the operating parameter is identified based on the temporal status and on the categorization of the arrhythmia. The temporal status can track the amount of time since a status event, which status event can correspond to a medical event, a treatment, or the like. In some embodiments, the event can be inputted to the system by the patient and/or by a clinician treating the patient. In some embodiments, the temporal status can be determined based on a fixed amount of time since the status event, and in some embodiments, the temporal status can be determined based on a variable amount of time since the status event. In some embodiments, for example, the amount of time can be changed and/or reset by the patient and/or other individual based on one or several attributes of the patient. In some embodiments, the temporal status is indicative of an amount of time elapsed since implantation of the blood pump. In some embodiments, a magnitude of the adjustment to the operating parameter of the blood pump decreases as the amount of time elapsed since implantation of the blood pump increases.

In some embodiments, the categorization of the arrhythmia identifies an arrhythmia type or an arrhythmia severity. In some embodiments, the arrhythmia type can include at least one of: an atrial fibrillation; premature ventricular contractions; ventricular fibrillation; and ventricular tachycardia. In some embodiments, the arrhythmia severity is determined based on at least one of: a duration of the arrhythmia; a ventricular rate; and one or several ventricular/supraventricular tachycardia discriminator values. In some embodiments, these one or several ventricular/supraventricular tachycardia discriminator values can include, for example, morphology of the electrical signal, regularity of the arrhythmia, suddenness of the arrhythmia onset, or the like. In some embodiments, the adjustment to the operating parameter of the blood pump includes at least one of: incrementing a speed of the blood pump; and decrementing the speed of the blood pump. In some embodiments, the adjustment to the operating parameter of the blood pump can include changing a pumping operation mode. In some embodiments, the pumping operation mode can include at least one of: pulsatile pumping; or continuous pumping.

In some embodiments, the processor can: determine a current operating parameter of the blood pump; retrieve a threshold value based on the current operating parameter and compare a speed of the blood pump operating at the adjusted operating parameter to the threshold value. In some embodiments, the threshold value delineates between acceptable speeds of the blood pump and unacceptable speeds of the blood pump. In some embodiments, the processor can control the blood pump to operate at the speed corresponding to the threshold value when the speed of the blood pump operating at the adjusted operating parameter exceeds the threshold value.

BRIEF DESCRIPTION OF THE DRAWINGS

Further details, aspects, and embodiments of the invention will be described by way of example only and with reference to the drawings. In the drawings, like reference numbers are used to identify like or functionally similar elements. Elements in the figures are illustrated for simplicity and clarity and have not necessarily been drawn to scale.

FIG. 7 is a depiction of one exemplary embodiment of a lookup table for controlling operation of a blood pump.

DETAILED DESCRIPTION

Figure 1:
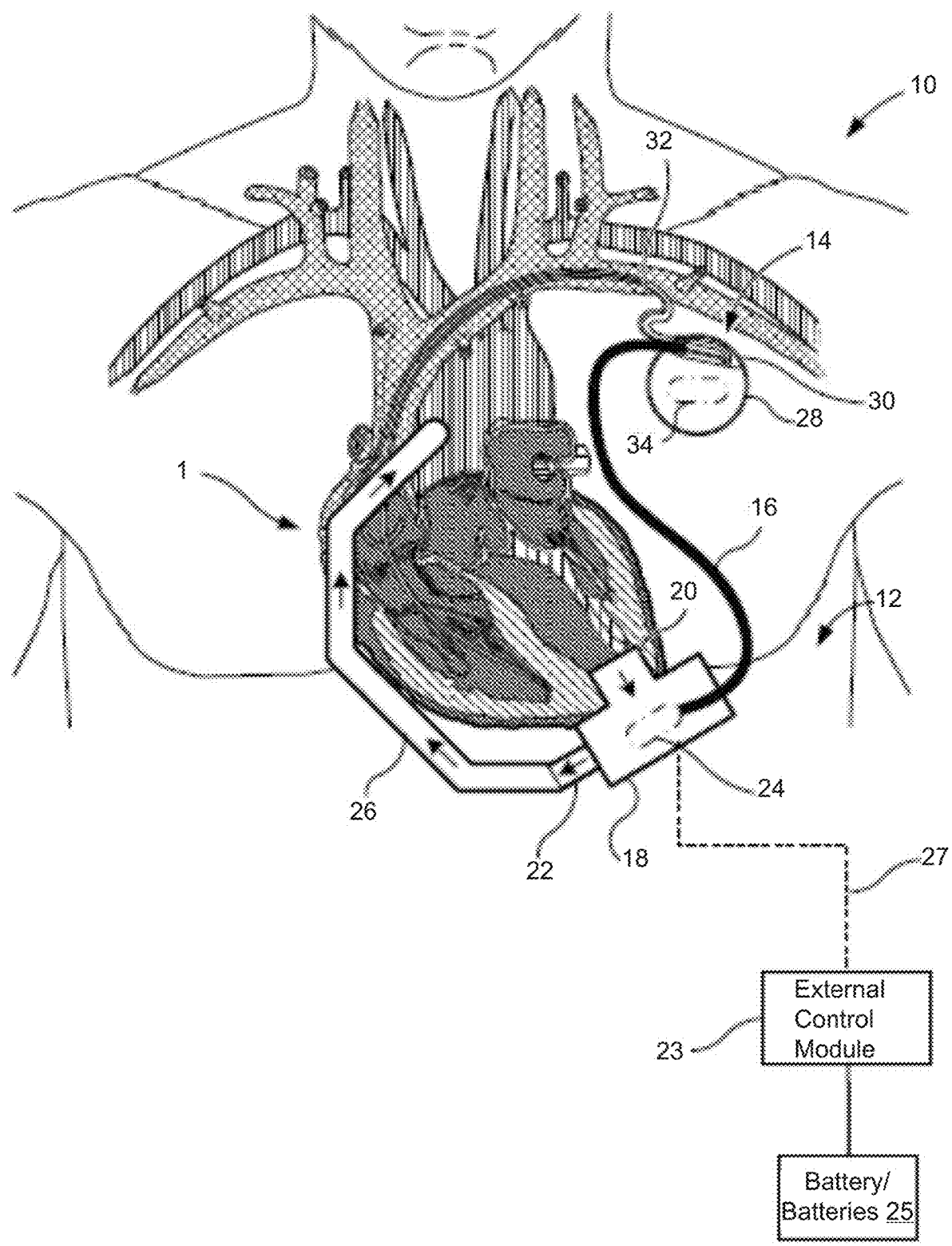
FIG. 1 illustrates an exemplary system of the present invention.

The present invention generally relates to heart assist systems and in particular methods and systems for modifying operation of an implantable blood pump according to information communicated between an implantable blood pump and an implantable cardiac rhythm management device. This information can be used to, for example, change pump speed to diminish strain placed on a heart by the blood pump and/or to compensate for diminished blood flow during an arrhythmia, and/or to prepare and/or improve one or several attributes of tissue of the heart, the heart, and/or tissue surrounding the heart for receipt of an electrical treatment which can include any treatment in which a current and/or voltage is applied to all or portions of the heart including, for example, an electroshock treatment, also referred to herein as an electroshock therapy, electroshock defibrillation, and/or electrical impulses.

In some embodiments, the degree to which pump speed is changed can depend on several factors including, for example, the detected arrhythmia, the severity of the detected arrhythmia, a temporal status, they can be, for example, indicative of an amount of time elapsed since implantation of a medical device, such as, for example, a blood pump, or the like. Different types of arrhythmias can present in a heart. These can include, for example, atrial fibrillation, ventricular tachycardia, ventricular fibrillation, atrial flutter, and premature ventricular contraction. In addition to having different symptoms, these different arrhythmias can have different short-term and long-term risks.

Further, each of these different arrhythmias may have different severities. The severities can be characterized by, for example, a ventricular rate and/or a duration of the arrhythmia. Thus, a patient can be diagnosed as being affected by a type of arrhythmia having a specific or determined severity. Like the different arrhythmias, the different severities of arrhythmia can have different short or long-term consequences and/or risks.

In addition to the arrhythmia type and severity providing insights into arrhythmia risks, a temporal status can likewise provide insights into risks associated with an arrhythmia. Subsequent to the implantation of a medical device such as a blood pump in the patient, the frequency and severity of arrhythmias can increase during a period in which the patient's body adapts to the blood pump. These arrhythmias can immediately decrease cardiac output and can have long-term detrimental effects on cardiac output. Some of these arrhythmias can even be immediately life-threatening. It has been observed that the patient's body adapts to implantation of the medical device and the frequency and severity of arrhythmias decreases after approximately one to three months.

By controlling pump speed in response to information indicative of arrhythmia type, severity, and temporal status, short and long-term risks and consequences of the arrhythmias can be mitigated and patient outcomes can be improved. This control can be achieved, in some embodiments, by adjustment of the pump speed, according to information stored within memory linking one or several arrhythmias, arrhythmia severities, and/or temporal statuses to one or several pump speed and/or to one or several pump speed adjustments. In some embodiments, information on appropriate adjustment speed and mode for each scenario can be stored in a database, a lookup table, or the like.

In addition to controlling pump speed to counteract diminished cardiac output, pump speed can be controlled to manage all or portions of the cardiac environment in preparation for delivery of electroshock therapy. In some embodiments, for example, information communicated from the implantable cardiac rhythm management device to the implantable blood pump can identify an impending electroshock therapy. Based on this information communicated between the implantable blood pump and the implantable cardiac rhythm management device, the speed of the blood pump can be changed to affect one or several electrical properties of all or portions of the heart in preparation for delivery of electroshock therapy. This can include, for example, affecting impedance in all or portions of a heart, and specifically affecting impedance in tissue of the heart and/or portions of the heart spanned by the cardiac defibrillator shock vector.

In some embodiments, this can include reducing the impedance of all or portions of the heart and specifically of tissue spanned by the shock vector. This reduction in impedance can reduce the amount of energy required to defibrillate the heart by the implantable cardiac rhythm management device that can include, for example, an implantable cardioverter defibrillator ("ICD"). This reduction in energy required to defibrillate the heart can increase the life of the battery of the implantable cardiac rhythm management device. The increased life of the battery of the implantable cardiac rhythm management device can allow a longer interval before removal and replacement of the implantable cardiac rhythm management device is required, which longer interval can minimize risks associated with the removal and replacement of the implantable cardiac rhythm management device to which the patient is exposed.

In some embodiments, the pump speed can be controlled to both counteract diminished cardiac output and to manage all or portions of the cardiac environment in preparation for delivery of electroshock therapy. In some such embodiments, this control of the pump can include, for example, controlling pump speed to counteract diminished cardiac output, adjusting the pump speed to manage all or portions of the cardiac environment in preparation for delivery of electroshock therapy, and returning to controlling pump speed to counteract diminished cardiac output based on the effectiveness of the electroshock therapy. In some embodiments, these different treatments can be simultaneously provided, or serially provided.

Thus, control of the pump according to information communicated between the implantable blood pump and the implantable cardiac rhythm management device can improve patient outcomes and decrease both short and long-term risks to which the patient is exposed. One system for communication of such information is shown in FIG. 1. FIG. 1 illustrates an exemplary heart treatment or support system 10 of the present invention. As used herein, "heart treatment system," "heart support system," and "cardiovascular system" are used somewhat interchangeably.

Heart treatment system 10 includes an implantable blood pump 12 and a cardiac electronic device 14 which can be an implantable cardiac rhythm management device 14. In some embodiments, the cardiac rhythm management device 14 can be, for example, an IPM, an ICD, a CRT device, one or several monitoring systems or devices such as a pulmonary arterial pressure ("PAP") sensor and/or a CardioMEMS, or the like. In some embodiments, the sensor can include, an implantable, battery-free sensor. In some embodiments, this sensor can be implanted into the distal pulmonary artery and can measure, or specifically can continuously measure one or several heart attributes including, for example, the heart rate, the systolic blood pressure, the diastolic blood pressure, and/or the mean blood pressure. Exemplary embodiments of some such sensors are disclosed in U.S. Pat. No. 6,855,115, the entirety of which is hereby incorporated by reference herein. In various embodiments, the blood pump refers to a ventricular assist system including a pump, battery, and peripherals. In various respects, "heart treatment system" can be used to refer to one or more cardiovascular systems. In one example, heart treatment system refers to a combined system including two subsystems: a left ventricular assist system and a cardiac rhythm management system.

In some embodiments, the implantable blood pump 12 and the implantable cardiac rhythm management device 14 may be wired or wirelessly communicatingly coupled to one another. In some embodiments, this communicating coupling can be direct such that the implantable blood pump 12 and the implantable cardiac rhythm management device 14 directly communicate with each other, and in some embodiments, this communicating coupling can be indirect such that each of the implantable blood pump 12 and the implantable cardiac rhythm management device 14 can communicate with a control module 23, also referred to herein as controller 23, discussed below.

In the embodiment depicted in FIG. 1, the implantable blood pump 12 and the implantable cardiac rhythm management device 14 are operatively coupled to one another by a communication line 16 to share information between the implanted devices. In some embodiments, the implantable cardiac rhythm management device 14 may send information to the implantable blood pump 12 through the communication line 16. In other embodiments, the implantable blood pump 12 may send information to the implantable cardiac rhythm management device 14 through the communication line 16. And in further aspects, information may be passed from the implantable cardiac rhythm management device 14 to the implantable blood pump 12 and vice-versa.

The blood pump 12 may be configured to couple with the circulatory system (e.g., heart 1) of the patient and to assist in pumping blood therethrough. In some embodiments, the pump 12 includes a pump housing 18 and an inlet cannula 20 and an outlet 22 extending from the housing 18. In some embodiments, the pump 12 may further include the control module 23. The control module 23 can be an external control module that can be located outside the patient's body, or an internal control module that can be implanted within the patient's body. In some embodiments, the pump can be configured similar to an LVAD described in U.S. Patent Publication 2015/0290374; U.S. Patent Publication 2014/0188148; U.S. Pat. Nos. 9,091,271; 8,794,989, 8,682,431; 8,894,561; and/or 9,091,271, the contents of which are incorporated herein by reference in their entirety.

The housing 18 may house a rotor of the blood pump 12 an may also include on-board electronics 24 (e.g., processor, battery, sensors, memory, communications module, etc.). The inlet cannula 20 may be configured to couple with a chamber of the heart 1 and the rotor of blood pump 12 may draw blood from a coupled heart chamber and output blood through output 22. The output 22 of the pump 12 may couple with a vascular graft assembly 26 which may be coupled with another portion of the patient's circulatory system (e.g., aorta, or the like) to deliver the pumped blood back into the circulatory system of the patient.

In some embodiments, the controller 23 can receive data from the blood pump 12 and/or from the implantable cardiac rhythm management device 14. The data received from the pump 12 can include information relating to one or several operating parameters of the blood pump 12 such as, for example, a speed, also referred to herein as a pump speed of the blood pump 12, or a pump operating mode. In some embodiments, the pump operating mode can be pulsatile pumping of continuous pumping. The controller 23 can send commands to the blood pump 12, including, for example, commands to change and/or adjust the operating parameter of the blood pump 12, and in some embodiments, to change and/or adjust the pump speed of the blood pump 12. In some embodiments, these commands can be in the form of a command to increment and/or decrement the pump speed of the blood pump by some predetermined value, and in some embodiments, these commands can be in the form of a command to change the pump speed to a desired pump speed. The control module 23 may be wired or wirelessly communicatingly coupled with the pump 12. As depicted in FIG. 1, the control module 23 is coupled with the blood pump 12 by a percutaneous cable 27. In some embodiments, one or more batteries 25 may be coupled with the control module 23 to power the control module 23. The batteries 25 may be external batteries or internal batteries 25.

Figure 2:
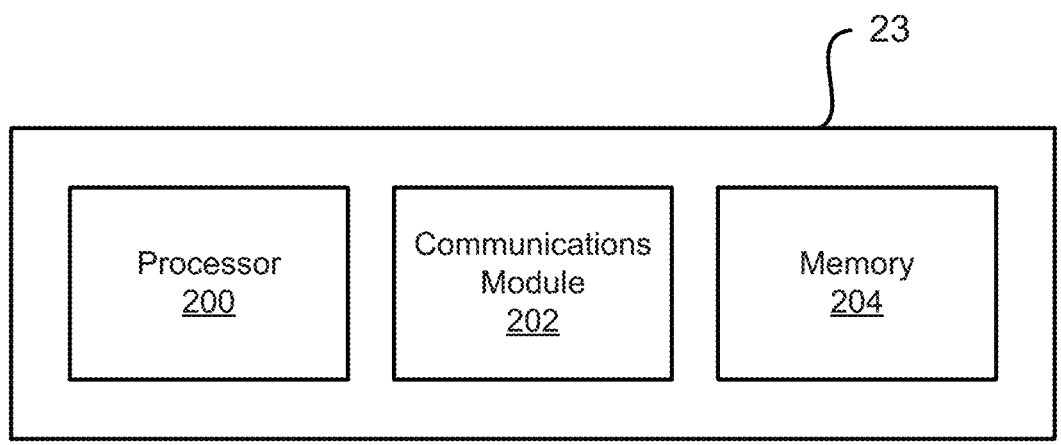
FIG. 2 is a schematic illustration of one embodiment of the controller.

In some embodiments, the control module 23 may comprise on-board electronics which can include, for example, as depicted in FIG. 2, a processor 200, communication module 202 including an antenna, transceiver, a transmitter, and/or a transceiver, a memory 204, or the like. The processor 200 can provide instructions to and receive information from the blood pump 12 and the implantable cardiac rhythm management device 14. The processor 200 can act according to stored instructions, which stored instructions can be located in the memory 204, and the processor 200 can, in accordance with stored instructions, make decisions. The processor 200 can comprise a microprocessor, such as a microprocessor from Intel® or Advanced Micro Devices, Inc.®, or the like.

The memory 204 can store information for use in controlling the operation of the blood pump 12 via the delivery of one or several commands from the control module 23 to the blood pump 12. In some embodiments, the memory 204 can store information for use in controlling the implantable cardiac rhythm management device 14 via one or several commands from the control module 23 to the implantable cardiac rhythm management device 14. In some embodiments, the memory 204 can include one or several algorithms for use in analyzing information received from one or both of the blood pump 12 and the implantable cardiac rhythm management device 14 and for controlling the blood pump 12 and/or the implantable cardiac rhythm management device 14.

In some embodiments, the memory 204 can include an algorithm for controlling the blood pump 12 based on information relating to one or several impending electrical treatments, and in some embodiments, the memory can comprise information for controlling the blood pump 12 based on information relating to one or several arrhythmias. In some embodiments, for example, the memory can include a database and/or lookup table comprising information categorizing one or several arrhythmias and a pump speed and/or pump speed adjustment associated with the categorized arrhythmias.

The communications module 202 can include one or several hardware or software components to enable communication between the controller 23 and the blood pump and/or between the controller 23 and the implantable cardiac rhythm management device 14. These features can include, for example, one or several antennas, one or several transmitters, receivers, and/or transceivers, or the like. In some embodiments, and as discussed above, the communication can be wired via, for example, the percutaneous cable 27 and/or the communication line 16, or wireless.

While pump 12 is generally illustrated as a centrifugal pump, it should be understood that the communications systems and methods described herein are not limited to centrifugal pumps, but are equally applicable to other pump designs (e.g., axial flow or mixed flow, etc.). Additionally, while pump 12 is illustrated as supporting the left ventricle, it should be understood that the pump 12 may be coupled with other portions of the heart 1, such as the right ventricle or other chambers of the heart 1, or other catheter or intravascular pump systems that couple to cardiovascular locations (e.g., descending aorta and other intravascular placements).

The implantable cardiac rhythm management device 14 may be configured to couple with one or more portions of the heart 1 of the patient to pace, resynchronize, and/or sense electrical activity of the heart 1. In some embodiments, the device 14 can be configured similar to a devices described in U.S. Pat. Nos. 8,180,448; 8,295,939; 8,543,205; 7,945,333; 8,295,939; 7,853,325; 8,145,324; 8,180,448; 8,224,462; 8,364,283; 8,712,544; 8,897,887; 7,245,117; 7,439,723; 7,498,799; 7,550,978; 7,679,355; 7,839,153; 6,111,520; and/or 6,278,379, the contents of which are incorporated herein by reference in their entirety. In some embodiments, the implantable cardiac rhythm management device 14 may include a housing 28, a header 30, and one or more leads 32.

The housing 28 may house on-board electronics 34 of the implantable cardiac rhythm management device 14 (e.g., processor, sensor(s), battery, etc.). The header 30 may provide an interface between the electronics 34 and the one or more leads 32 extending from the housing 28.

The one or more leads 32 may operably couple the implantable cardiac rhythm management device 14 to the heart 1 of the patient for pacing, resynchronizing, and/or sensing electrical activity of the heart 1. The one or more leads 32 may couple the implantable cardiac rhythm management device 14 to the right ventricle, right atrium, left ventricle, and/or the left atrium depending on the type of implantable cardiac rhythm management device 14 and treatment needed. Additionally, while generally illustrated as coupling, e.g., via leads, with the endocardium, the implantable cardiac rhythm management device 14 may be configured to couple with portions of the epicardium to carry out its functions.

Communication line 16 may couple the implantable blood pump 12 and/or the control module 23 with the implantable cardiac rhythm management device 14 so that information may be shared from one implant to the other. For example, the communication line 16 may have a first end that couples to the on-board electronics 34 of the implantable cardiac rhythm management device 14 and a second end that couples to the on-board electronics 24 of the implantable blood pump 12 and/or to the controller 23. In some embodiments, the first end connects to the on-board electronics 34 of the implantable cardiac rhythm management device 14 through an open through-hole or plug in the header of the implantable cardiac rhythm management device 14.

In some embodiments, the communication line 16 provides an electrical connection between the implantable blood pump 12 and the implantable cardiac rhythm management device 14. Optionally, the communication line 16 may be a lead that may be similar in configuration to the one or more leads 32. As such, the communication line 16 may couple to the on-board electronics 34 of the implantable cardiac rhythm management device 14 through the header 30. The on-board electronics 34 of the implantable cardiac rhythm management device 14 may include a sensor (e.g., activity sensor, accelerometer, timers) for estimating physical exertion by the patient and/or the time of day. The frequency of heart stimulation pulses 100 may be increased during higher activity (e.g., walking) and/or day time and lowered during lower activity (e.g., sleeping or resting) and/or night time.

In certain embodiments, the communication line 16 may provide an optical connection between the implantable blood pump 12 and the implantable cardiac rhythm management device 14. An optical connection may be desirable in some situations because the optical cable may be more resistant to corrosion and infection during long term implantation of the implant 14 and may be faster and higher resolution signaling, compared to an implant using an electrical connection. However, an electrical connection may be beneficial in some situations as fewer modifications are required to existing implantable cardiac rhythm management devices.

As set forth above, the heart treatment system 10 may improve patient treatment due to information shared between the implanted devices 12, 14, which information can be used to affect operation of the blood pump 12 to counteract detrimental effects of an arrhythmia and/or to improve the effectiveness of an electrical treatment. In some embodiments, the implantable cardiac rhythm management device 14 may be configured to deliver heart stimulation pulses to the heart 1 of the patient to pace the patient's heart 1 and/or to defibrillate the heart.

In some embodiments, in addition to delivering heart stimulation pulses to the heart 1 of the patient, and as discussed above, the implantable cardiac rhythm management device 14 may also be configured to deliver information to the blood pump 12 and/or to the controller 23. This information can be indicative of attributes of the heart such as, for example, the presence of one or several arrhythmias and/or the severity of those one or several arrhythmias. In some embodiments, this information can indicate an impending electrical treatment.

The pump processor of the implantable blood pump 12 and/or the processor 200 of the controller 23 may be configured to receive the information from the implantable cardiac rhythm management device 14 and may adjust an operational parameter such as a pump speed of the implantable blood pump 12 based on the received information. In some embodiments, the implantable blood pump 12 can be controller to provide additional pumping in response to receipt of the information. Similarly, the implantable blood pump 12 may decrease pumping in response to the receipt of the information. As such, the implantable blood pump 12 may leverage one or more activity sensors of the implantable cardiac rhythm management device 14 to adjust pumping.

The one or more activity sensors may comprise electrical pulse detection (e.g., heart rate sensing), one or more accelerometers, time stamp information for time of day information, etc.

In some embodiments, the implantable cardiac rhythm management device 14 can be configured to sense electrical signals from the heart 1 and the implantable cardiac rhythm management device 14 can detect and/or diagnose an abnormal heart rhythm of the patient based on the sensed electrical signals. The implantable cardiac rhythm management device 14 can, in response to the detection of the abnormal heart rhythm, generate and send a communication to the blood pump 12 and/or the controller 23 indicating the abnormal heart rhythm and/or one or several attributes of the abnormal heart rhythm. In some embodiments, this communication can include identification of the diagnosed abnormal heart rhythm of the patient. In some embodiments, these signals can, for example, be in the form of a unique series of electrical pulses that may be associated with the specific type of abnormal heart rhythm detected by the implantable cardiac rhythm management device 14. In some embodiments, the series of electrical pulses comprise a series of simple square wave signals. This may be advantageous in reducing power requirements of the communications method.

The pump processor and/or the processor 200 of the controller 23 may receive the unique series of electrical pulses and may decode the unique series of electrical pulses to determine the type of abnormal heart rhythm being experienced by the patient. In response, the pump processor and/or the controller 23 may be configured to adjust and implement a pumping protocol of the implantable blood pump 12 to account for the abnormal heart rhythm and/or to determine an adjustment to the operating parameter of the blood pump 12. For example, in some embodiments, the pump processor may temporarily speed and/or slow operation of the pump in the event that fibrillation of the heart is sensed. The pump 12 may, in some embodiments, revert to the pervious pump speed after the fibrillation of the heart has terminated and/or after delivery of an electrical treatment.

In some embodiments, the pump processor may decode the received unique series of electrical pulses using a database and/or lookup table. For example, the processor may compare the received series of electrical pulses to a database that stores a plurality of different possible signals and associates each of these possibilities with a type of abnormal heart rhythm. By identifying a match between the received signal and the signal stored in the database, the pump processor may then match the received signal with a specific type of abnormal heart rhythm signaled by the implantable cardiac rhythm management device 14. Alternatively, in some embodiments, the pump processor may determine extract information identifying the diagnosis of the abnormal heart rhythm from the communication received from the implantable cardiac rhythm management device 14.

Figure 3:
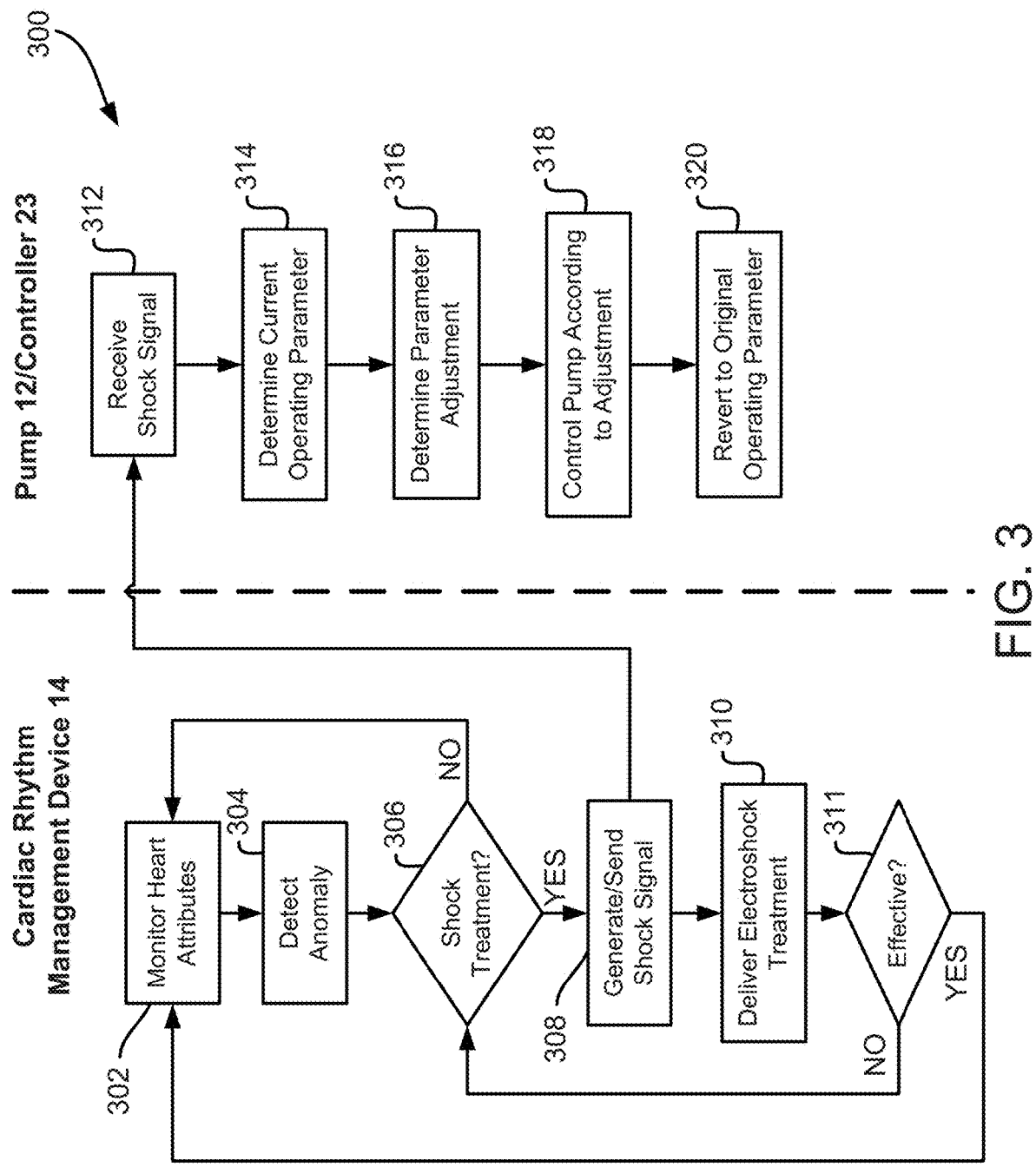
FIG. 3 is a swim lane diagram of one embodiment of a process for controlling a blood pump.

With reference now to FIG. 3, a swim lane diagram of one embodiment of a process 300 for controlling a blood pump 12 is shown. In some embodiments, the process 300 can increase the battery life of an implantable cardiac rhythm management device 14, can increase the time in which the implantable cardiac rhythm management device 14 can remain in vivo, and can improve the effectiveness of a delivered electrical treatment. As depicted in FIG. 3, the process 300 can be performed by the cardiac rhythm management device 14 and the pump 12 and/or the controller 23. In some embodiments, the process 300 can be performed by the on-board electronics 34 of the cardiac rhythm management device 14, the on-board electronics 24 of the pump 12, and/or the processor 200 of the controller 23.

The process 300 begins at block 302 wherein heart attributes are monitored. This can include the monitoring of all or portions of the heart for indicia of an arrhythmia. This monitoring can be performed by the cardiac rhythm management device 14. As indicated in block 304 of the process 300, an anomaly in the function of the heart, such as an arrhythmia, can be detected by the cardiac rhythm management device 14. In some embodiments, the detection of this arrhythmia can include, as indicated in decision state 306, determining whether the arrhythmia is sufficient to warrant electrical treatment such as a defibrillation. In some embodiments, this determination can include determining whether the arrhythmia is sufficiently severe and/or has a sufficient duration to warrant electrical treatment. If it is determined that electrical treatment is not warranted, then the process 300 can return to block 302 and continue as outlined above.

If it is determined by the cardiac rhythm management device 14 and specifically by the on-board electronics 34 of the cardiac rhythm management device 14 that electrical treatment is warranted, then the process 300 proceeds to block 308 wherein a signal which can indicate an impending shock and which can, in some embodiments, comprise an indicator of an impending shock, is generated and/or sent. The signal and/or indicator can be generated and/or sent by the on board electronics 34 of the cardiac rhythm management device 14 to the pump 12 and/or to the controller 23. In some embodiments, simultaneous with the generating and sending of a shock signal, a timer can be started, which timer can track the amount of time elapsed since the generating and/or sending of the signal and/or indicator. In some embodiments, for example, the electrical treatment can be delivered after a predetermined amount of time, also referred to herein as after a second period of time, has elapsed since the generating and/or sending of the signal and/or indicator. In some embodiments, this second period of time can have a length of: less than 1 second, approximately 1 second, approximately 2 seconds, approximately 5 seconds, approximately 10 seconds, approximately 15 seconds, approximately 20 seconds, approximately 30 seconds, approximately 45 seconds, approximately 60 seconds, between 1 and 10 seconds, between 1 and 20 seconds, between 1 and 40 seconds, between 1 and 60 seconds, between 1 and 120 seconds, between 1 and 240 seconds, and/or any other or intervening length of time. The passing of this predetermined amount of time can be determined based on the timer started with the generating and sending of the signal and/or indicator indicative of the impending electrical treatment.

After the generating and sending of the signal and/or indicator indicative of the impending electrical treatment, the process 300 proceeds to block 310 wherein the electrical treatment is delivered. In some embodiments, the electrical treatment can be delivered after the passing of the predetermined amount of time subsequent to the generating and/or sending of the signal and/or indicator of the impending electrical treatment, the electrical treatment can be delivered subsequent to determining a change in an attribute of all or portions of a heart, such as, for example, a decrease in impedance of all or portions of a heart, and/or the electrical treatment can be delivered subsequent to receipt of a signal and/or indicator from the pump 12 and/or controller 23 indicative of readiness for delivery of the electrical treatment. In some embodiments, for example, the impending electrical treatment is delivered after the impedance of the heart tissue is substantially affected according to the detection of impedance change, based on an output signal transmitted from the heart pump, or after a second period of time.

In some embodiments, the signal and/or indicator indicative of readiness for delivery of the electrical treatment can include a signal or indicator indicating the controlling of one or several operational parameters of the pump 12 in preparation for the delivery of the electrical treatment. In some embodiments in which the controlling of the blood pump 12 affects an attribute of the heart, the amount of energy delivered in the electrical treatment can be adjusted as the attribute of the heart is affected. In some embodiments, for example, as the impedance of all or portions of the heart decreases, the amount of energy required to effectively deliver the impending electrical treatment decreases. In such an embodiment, the amount of energy delivered as part of the electrical treatment can be reduced based on the reduced impedance of the heart tissue to be affected by the impending electrical treatment.

After the electrical treatment has been delivered, the process 300 proceeds to decision state 311, wherein it is determined if the delivered electrical treatment was effective. In some embodiments, this can include determining whether the delivered electrical treatment terminated the arrhythmia. In some embodiments, this can include determining whether the delivered electrical treatment completely terminated the arrhythmia and/or sufficiently terminated the arrhythmia. If it is determined that the delivered electrical treatment was ineffective, then the process 300 returns to block 306 and proceeds as outlined above. If it is determined that the delivered electrical treatment was effective, the process 300 can return to block 302 and proceed as outlined above.

Returning again to block 308, in some embodiments, the signal and/or indicator indicative of the impending electroshock can be sent to the pump 12 and/or the controller 23 and can be received as indicated in block 312. In some embodiments, the shock signal can be received by the communications module 202 of the controller 23, and/or by a module of the pump 12 that is similar to the communications module 202. In some embodiments, a timer can be started with receipt of the shock signal. This timer can track the amount of lapsed time since receipt of the shock signal and can be used to determine when to revert to original operating parameters of the blood pump 12.

After the shock signal and/or indicator has been received, the process 300 proceeds to block 314 wherein a current operating parameter of the blood pump 12 is determined. In some embodiments, this operating parameter can be indicative of one or several aspects of the operation of the blood pump 12. In some embodiments, this can include, determining the current pump speed of the pump 12. In some embodiments, this determination can be made by the processor 200 by querying the pump 12 for information identifying the current pump speed, and in some embodiments, this determination can be made by the processor 200 by retrieving the most recent control signals sent to the pump 12, which control signals comprise at least one operating parameter identifying a desired pump speed.

After determining the current operating parameter of the blood pump 12, the process 300 proceeds to block 316, wherein a parameter adjustment is determined. In some embodiments, the parameter adjustment can be generic, in some embodiments, the parameter adjustment can be specific to the blood pump. In some embodiments, information identifying the adjustment can be stored in the memory 204.

The parameter adjustment can be configured to change an operating parameter of the blood pump 12 to improve the effectiveness of the electrical treatment, and specifically to reduce the amount of energy required to deliver an effective electrical treatment. In some embodiments, this improvement in the effectiveness of the electrical treatment can be achieved by increasing and/or decreasing the pump speed, which changes the blood flow rate through the patient's heart that thereby affect an impedance of all or portions of the heart. In some embodiments, for example, the adjustment can be configured to affect blood flow through the heart and specifically to increase the amount of blood in the patient's heart to thereby decrease impedance across all or portions of the heart.

After the adjustment parameter has been determined, the process 300 proceeds to block 318, wherein the blood pump 12 is controlled according to the determined adjustment. In some embodiments, the blood pump 12 can be controlled for a first period of time based on at least the adjustment determined in block 316 to affect the impedance of the heart tissue to be affected by the impending electrical treatment. In some embodiments, this first time period can be a predetermined time period with a length of, for example, less than 1 second, approximately 1 second, approximately 2 seconds, approximately 5 seconds, approximately 10 seconds, approximately 15 seconds, approximately 20 seconds, approximately 30 seconds, approximately 45 seconds, approximately 60 seconds, between 1 and 10 seconds, between 1 and 20 seconds, between 1 and 40 seconds, between 1 and 60 seconds, between 1 and 120 seconds, between 1 and 240 seconds, and/or any other or intervening length of time. In some embodiments, the first time period can extend until a signal is received from the cardiac rhythm management device 14 indicating delivery of the electrical treatment, and in some embodiments, the first period can last until delivery of the electrical treatment is detected.

In some embodiments, the controlling of the blood pump 12 can include generating and sending one or several control signals from the controller 23 to the blood pump 12, which control signals can identify a change in one or several operating parameters of the pump according to the adjustment, which adjustment and which change can cause an increase and/or decrease in the pump speed. In embodiments in which the adjustment specifies both an increase and/or decrease in the pump speed, the control signals can be configured to create a biphasic pulse by one of either initially increasing or decreasing the speed of the blood pump followed by the other of increasing or decreasing the speed of the blood pump. In some embodiments, for example, the speed of the blood pump will be initially increased followed by a sudden decrease in the pump speed. It is believed that such a biphasic pulse may increase the volume of blood contained within the heart and may improve the effectiveness of the electrical treatment.

In some embodiments, and as indicated by broken arrow 319, the controller 23 and/or the blood pump 12 can communicate information relating to the control of the blood pump 12 to the device 14. In some embodiments, this communication can comprise information indicating the change in the pump operating parameter such as, for example, information indicating successful change in the pump speed. In some embodiments, this information can include a signal indicative of readiness for delivery of electrical treatment. In some embodiments, this information can identify one or several changes in attributes of all or portions of the heart, including indications of, for example, impedance of all or portions of the heart, changes in impedance in all or portions of the heart, or the like.

After the controlling the pump according to the adjustment, the process 300 can proceed to block 320 wherein control of the blood pump reverts to the original operating parameter or to any other desired operating parameter. In some embodiments, for example, control of the blood pump can revert to the original operating parameter after the passing of a predetermined amount of time, after a signal, indicated by broken arrow 313, indicative of the completion of the electrical treatment has been received, and/or after detection of delivery of the electrical treatment.

Figure 4:
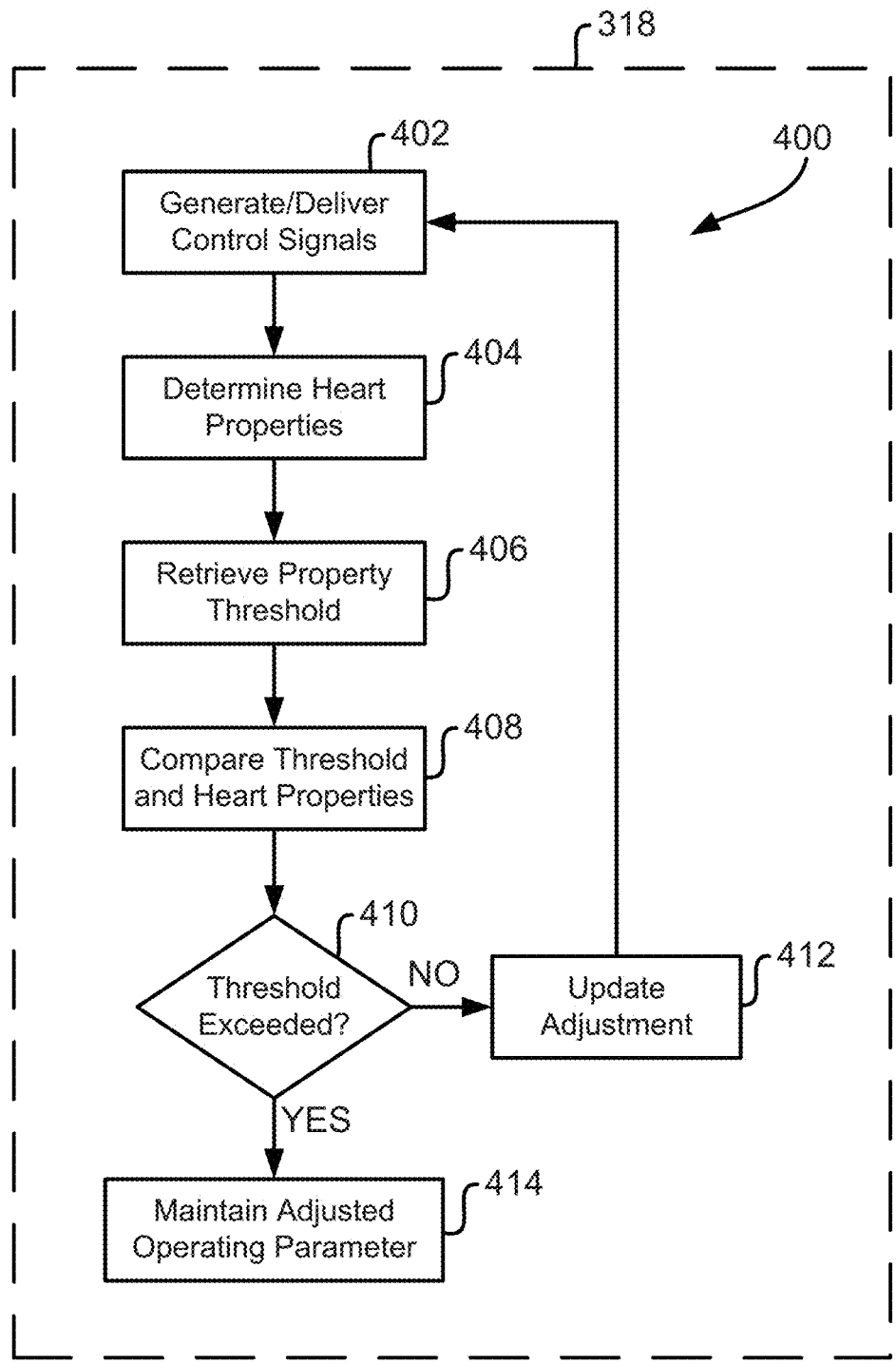
FIG. 4 is a flowchart illustrating one embodiment of a process for controlling blood pump.

With reference now to FIG. 4, a flowchart illustrating one embodiment of a process 400 for controlling blood pump 12, according to an adjustment is shown. In some embodiments, the process 400 can be performed as a part of or in the place of the step of block 318, showing FIG. 3. The process 400 can be performed by the pump 12 and/or by the controller 23. The process begins at block 402 wherein one or several control signals are generated and/or delivered. In some embodiments, these control signals can be generated by the on-board electronics 24 of the pump 12, and/or can be generated by the processor 200 of the controller 23 and sent to the pump 12 by the communications module 202 of the controller 23.

After the generating and sending of control signals, the process 400 proceeds to block 404 wherein one or several heart properties are determined. In some embodiments, this can include determining an impedance of all or portions of the heart. In some embodiments, these properties can be determined by the on board electronics 24 of the pump, and/or the processor of the controller 23. These properties can be determined based on information sent and/or gathered by the pump 12 and/or the controller, or alternatively based on information received from the implantable cardiac rhythm management device 14.

After the heart properties have been determined, the process 400 proceeds to block 406, wherein one or several threshold values associated with those properties are retrieved. In some embodiments, for example, one or several threshold values delineating between acceptable and unacceptable heart impedance values can be retrieved and/or one or several threshold values delineating between acceptable and unacceptable changes in a heart impedance values can be retrieved. In some embodiments, for example, a threshold value can identify an impedance value as acceptable when it is below a predetermined value, and/or the threshold value can identify a change in impedance as acceptable when the change in impedance decreases the impedance of all or portions of the heart by more than a predetermined value. In some embodiments, for example, a threshold value may identify a decrease of impedance of at least approximately 1%, of at least approximately 2%, of at least approximately 5%, of at least approximately 7%, of at least approximately 10%, of at least approximately 15%, of at least approximately 20%, of at least approximately 25%, of at least approximately 30%, of at least approximately 35%, of at least approximately 40%, of at least approximately 45%, of at least approximately 50%, of at least approximately 60%, of at least approximately 70%, of at least approximately 80%, of at least approximately 90%, or any other or intermediate decrease in impedance as acceptable. In some embodiments, these one or several values can be retrieved from memory of the on board electronics 24 of the pump 12, and/or can be retrieved from the memory 204 of the controller 23.

After the one or several threshold values have been retrieved, the process 400 proceeds to block 408, wherein the determined heart properties, and/or values characterizing the determined heart properties are compared to the retrieved one or several threshold values. And as indicated in decision state 410, it can be determined based on the comparison of the one or several thresholds and the one or several heart properties, if the one or several thresholds have been exceeded. If it is determined that one or several of the one or several thresholds has not been exceeded, then the process 400 can proceed to block 412, wherein the adjustment of the operating parameter of the blood pump is updated. In some embodiments, for example, this can include updating the adjustment to the operating parameter so as to further change the pump speed to thereby further change electrical property of all or portions of the heart. In some embodiments, the update to the adjustment can be selected and made to further decrease the impedance of all or portions of the heart to thereby achieve or come closer to achieving desired hard properties. After the adjustment has been updated, the process 400 returns to block 402 and proceeds as outlined above.

Returning to decision state 410, if it is determined that the threshold is exceeded, then the process 400 proceeds to block 414, wherein the adjusted operating parameter is maintained. In some embodiments, this can include maintaining the generation and delivering of control signals according to the parameter adjustment determined in block 316 of FIG. 3, and in some embodiments, this can include allowing the blood pump 12 to operate according to previously sent control signals.

Figure 5:
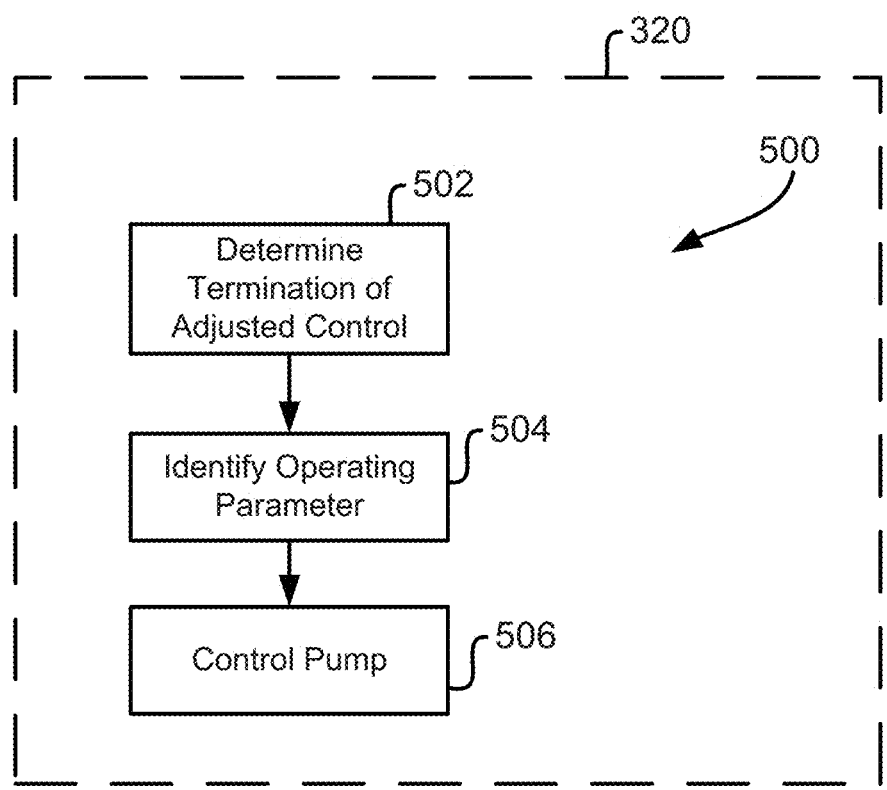
FIG. 5 is a flowchart illustrating one embodiment of a process for reverting to original operating parameters of the blood pump.

With reference now to FIG. 5, a flowchart illustrating one embodiment of a process 500 for reverting to original operating parameters of the blood pump 12 is shown. The process 500 can be performed as a part of or in place of the step of block 320 of FIG. 3. The process 500 can be performed by the blood pump 12, and specifically the on board electronics 24 of the blood pump 12, and/or by the controller 23, and specifically the processor 200 of the controller 23.

The process 500 begins at block 502 wherein a termination of adjusted control of the blood pump 12 is determined. In some embodiments, this determination can be determined based on, for example, the amount of elapsed time indicated by the timer started with receipt of the shock signal and 312, based on a communication received from the implantable cardiac rhythm management device 14 indicating successful delivery of electrical treatment, and/or based on detection of delivery of electrical treatment. In some embodiments, for example, the elapsed time for determining termination of adjusted control of the blood pump 12 can be, for example, less than 1 second, at least approximately 1 second, at least approximately 2 seconds, at least approximately 3 seconds, at least approximately 5 seconds, at least approximately 7 seconds, at least approximately 10 seconds, at least approximately 15 seconds, at least approximately 20 seconds, at least approximately 25 seconds, at least approximately 30 seconds, at least approximately 35 seconds, at least approximately 40 seconds, at least approximately 45 seconds, at least approximately 50 seconds, at least approximately 55 seconds, at least approximately 60 seconds, at least approximately 80 seconds, at least approximately 100 seconds, at least approximately 120 seconds, between 1 and 10 seconds, between 1 and 20 seconds, between 1 and 40 seconds, between 1 and 60 seconds, between 1 and 120 seconds, between 1 and 240 seconds, between 1 and 480 seconds, between 1 and 960 seconds, and/or any other or intermediate length or range of time. In some embodiments, detecting delivery of electrical treatment can include sense, intellectual attribute indicative of delivery of the electrical treatment or sensing of vibration, conduction, or movement indicative of delivery of the electrical treatment.

After the determination of termination of adjusted control, the process 500 proceeds to block 504, wherein an operating parameter is determined. This determined operating parameter can be the operating parameter that was in effect before the adjustment of the operating parameter in block 316 of FIG. 3. In some embodiments, for example, the operating parameter can be determined by identifying the operating parameter, which can be stored in the memory 200, used to control the blood pump 12 immediately before the adjustment of block 316 of FIG. 3. After the operating parameter has been determined, the process 500 proceeds to block 506, wherein the blood pump 12 is controlled. In some embodiments, the blood pump 12 can be controlled via the generating and/or sending of one or several control signals. In some embodiments, these control signals can be generated by the on-board electronics 24 of the pump 12. In some embodiments, for example, the processor 200 of the controller 23 can generate one or several control signals which can be sent to the blood pump 12 via the communications module 202 of the controller 23.

Figure 6:
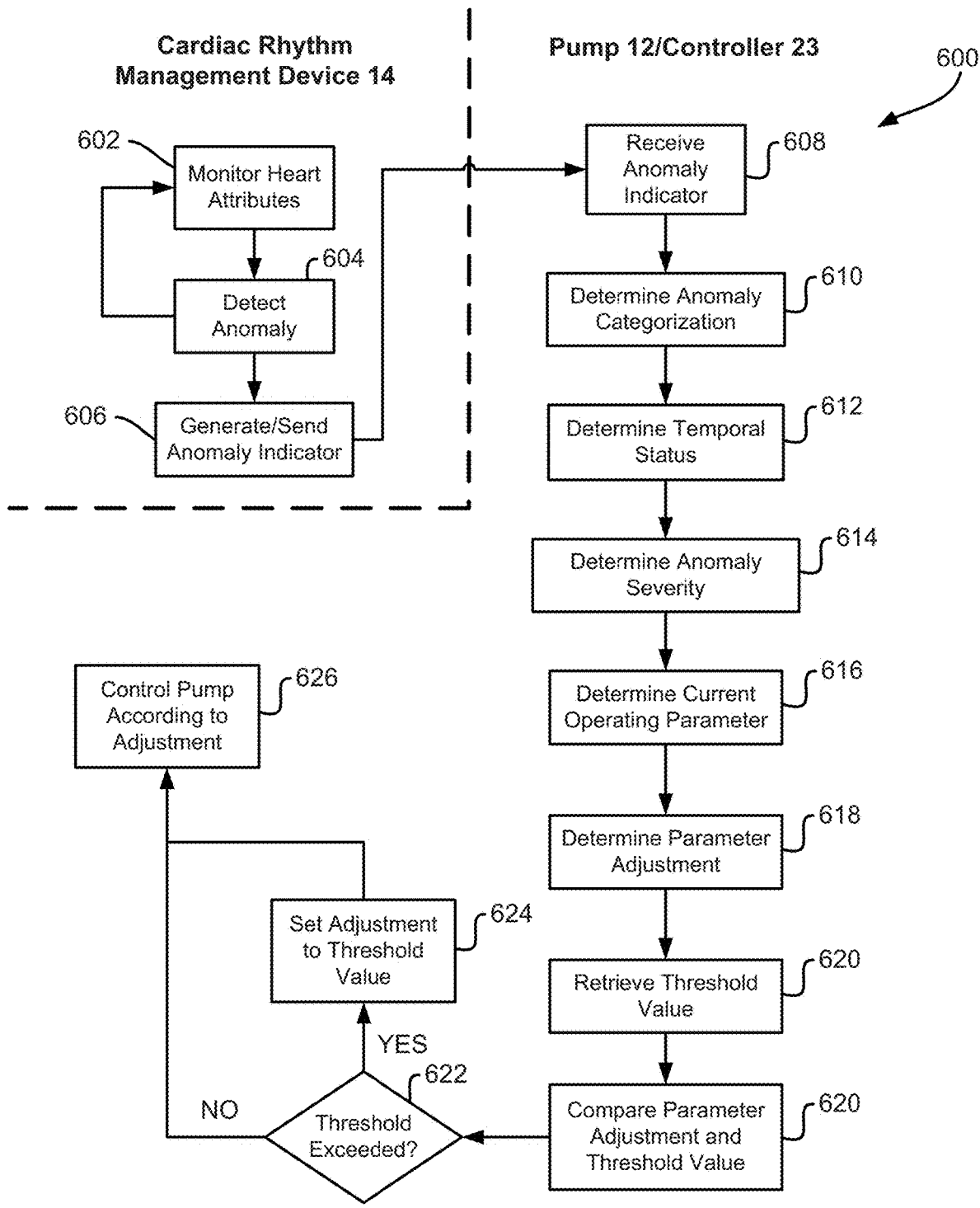
FIG. 6 is a swim lane diagram illustrating one embodiment of a process for delivering circulatory support.

With reference now to FIG. 6, a swim lane diagram illustrating one embodiment of a process 600 for delivering circulatory support is shown. In some embodiments, the process 600 can mitigate and/or eliminate adverse outcomes associated with arrhythmias, particularly in a critical period immediately subsequent to implantation of a heart related medical device. As depicted in FIG. 6, the process 600 can be performed by the cardiac rhythm management device 14 and the pump 12 and/or the controller 23. In some embodiments, the process 600 can be performed by the on-board electronics 34 of the cardiac rhythm management device 14, the on-board electronics 24 of the pump 12, and/or the processor 200 of the controller 23.

The process 600 can begin a block 602 wherein one or several heart attributes are monitored. This can include the monitoring of all or portions of the heart for indicia of an arrhythmia. This monitoring can be performed by the cardiac rhythm management device 14. As indicated in block 604 of the process 600, an anomaly in the function of the heart, such as an arrhythmia, can be detected by the cardiac rhythm management device 14. This detection can be performed by comparing the monitored heart attributes to criteria for identifying one or several arrhythmias. In some embodiments, the steps of block 602 and 604 can be repeatedly performed until an anomaly is identified, and/or can be continuously performed.

After an anomaly has been detected, the process 600 proceeds to block 606 wherein an anomaly indicator is generated and sent. In some embodiments, this can include the generation and sending of a signal from the cardiac rhythm management device 14 to the pump 12 and/or to the controller 23. In some embodiments, this indicator can include information such as a time and/or date stamp to allow identification of the time of occurrence of the anomaly and/or the duration of the anomaly. This signal can, in some embodiments, identify the detected anomaly and/or contain raw data indicative of the monitored heart attributes gathered as a part of step 602.

At block 608, the pump 12 and/or the controller 23 receives the anomaly indicator from the cardiac rhythm management device 14. In some embodiments, the anomaly indicator can be received by the communications module 202 of the controller 23. In some embodiments, a timestamp can be associated with the anomaly indicator indicating the time of receipt of the anomaly indicator by the pump 12 and/or controller 23 After receipt of the anomaly indicator, the process 600 proceeds to block 610, wherein an anomaly categorization is determined. In some embodiments, this can include determining a type of the anomaly such as, for example, determining that the anomaly comprises at least one of: an atrial fibrillation, a ventricular tachycardia ("VT"), a ventricular fibrillation ("VF"), an atrial flutter, and a premature ventricular contraction ("PVC"). In some embodiments, this determination can comprise the extraction of information from the anomaly indicator identifying the categorization of the anomaly, and in some embodiments, this determination can comprise analyzing data relating to heart attributes received in the anomaly indicator to determine the categorization of the anomaly.

After the anomaly categorization has been determined, the process 600 proceeds to block 612 wherein a temporal status is determined. In some embodiments, for example, the temporal status can identify a temporal proximity to an event, such as, for example, an implantation of a heart related medical device and/or an increase in policy of the blood pump. In some embodiments, for example, the implantation of a heart related medical device, such as the blood pump 12 can result in an increase in arrhythmias during a time period in which the body is adjusting to the presence of the blood pump. In anticipation of this increase in arrhythmias, in some embodiments, a temporal status can identify a time period such as, for example, one month, two months, three months, four months, six months, eight months, 12 months, or any other intervening time period immediately subsequent to the implantation of the heart related medical device. In some embodiments, the temporal status of this time period can be identified as acute.

In some embodiments, arrhythmias can increase subsequent to an increase of the speed of the blood pump 12. In anticipation of these increasing arrhythmias, in some embodiments, a temporal status can identify the time period such as, for example, one minute, two minutes, five minutes, 10 minutes, 30 minutes, one hour, two hours, six hours, 12 hours, one day, two days, three days, one week, two weeks, one month, two months, or any other intervening time period subsequent to an increase of the pump speed of the blood pump 12. In some embodiments, the temporal status of this time period can be identified as reactive and/or in response to a change in VAD pump speed such as, for example, an increase pump speed. In some embodiments, the temporal status outside of the acute or reactive statuses can be identified as chronic.

In some embodiments, the temporal status can be determined based on information contained in and/or associated with the anomaly indicator such as, for example, the time and/or date stamp and/or information identifying the time and/or date of the last event associated with a temporal status. In some embodiments, for example, information identifying the time and/or date of the implantation of a heart related medical device can be stored in the memory 204 or similarly, data identifying a time and/or date of a most recent change or increase in the pump speed can be stored in a memory 204. In some embodiments, information identifying time and/or date of temporal status associated events can be compared to time and/or date information associated with the anomaly indicator to determine the temporal status.

After the temporal status has been determined, the process 600 proceeds to block 614, wherein anomaly severity is determined. In some embodiments, the anomaly severity can be determined based on information indicating one or several attributes of the anomaly such as, for example, the ventricular rate and/or the duration of the anomaly. In some embodiments, for example, a threshold may delineate between ventricular rates classified as fast and ventricular rates classified as slow. In some embodiments, this threshold can identify 50 bpm, 75 bpm, 90 bpm, 100 bpm, 110 bpm, 120 bpm, 150 bpm, and/or any other or intermediate number beats per minute, as the threshold value delineating between fast and slow ventricular rates. In some embodiments, arrhythmia duration can include a threshold value delineating between arrhythmias having a long-duration and arrhythmias having a short duration. In some embodiments, for example, an atrial fibrillation can have a long duration when it lasts at least seven days, and atrial fibrillation can have a short duration if it lasts less than seven days. Similarly, in some embodiments, a PVC episode can have a long duration when more than one consecutive PVCs are detected. Likewise, in some embodiments, for example, a threshold may delineate between ventricular tachycardia and/or ventricular fibrillation classified as long duration and those classified as short duration. In some embodiments, this threshold can identify 6 intervals, 12 intervals, 18 intervals, 24 intervals, and/or any other or intermediate number of intervals, as the threshold value delineating between long and short durations.

After the termination of the anomaly severity, the process 600 proceeds to block 616, wherein the current operating parameter of the blood pump is determined. After the current operating parameter of the blood pump is determined, the process 600 proceeds to block 618 wherein a parameter adjustment is determined. In some embodiments, this can include querying a database and/or lookup table based on the anomaly categorization, temporal status, anomaly severity from steps 610 through 614 for a blood pump adjustment and/or an adjustment to the operating parameter. An embodiment of one such database and/or lookup table is shown in FIG. 7. In some embodiments, the parameter adjustment can specify a value for the operating value of the blood pump 12 such as, for example, a pump speed, and in some embodiments, the parameter adjustment can specify the incrementing and/or the decrementing of the pump speed. In some embodiments, this incrementing and/or decrementing of the pump speed can vary based on the determinations of block 610 through 614 such that, in some embodiments, a parameter adjustment may specify incrementing and/or the decrementing of the pump speed by 1 step, 2 steps, 3 steps, 4 steps, 5 steps, 6 steps, 7 steps, 8 steps, 9 steps, 10 steps, and/or any other or intermediate number of steps. In some embodiments, each of these steps may correspond to a predetermined change in pump speed such as, for example, an increase or a decrease in pump speed by: 1 or less rpm; by at least 1 rpm, by at least 2 rpm; 3 rpm, by at least 4 rpm, by at least 5 rpm, by at least 7 rpm, by at least 10 rpm, by at least 15 rpm, by at least 20 rpm, by at least 25 rpm, by at least 30 rpm, by at least 40 rpm, by at least 50 rpm, by at least 60 rpm, by at least 70 rpm, by at least 80 rpm, by at least 90 rpm, by at least 100 rpm, by at least 120 rpm, by at least 140 rpm, by at least 160 rpm, by at least 180 rpm, by at least 200 rpm, by at least 240 rpm, by at least 260 rpm, by at least 280 rpm, by at least 300 rpm, and/or any other or intermediate pump speed.

At block 620 of the process 600, one or several threshold values is retrieved. In some embodiments, the threshold value can delineate between acceptable and unacceptable pump speeds. In some embodiments, for example, the blood pump 12 can have a maximum and/or a minimum operating speed. The maximum and/or minimum operating speeds can be defined by the retrieved one or several threshold values. The threshold values can be retrieved from, for example, the memory 204. After the threshold value has been retrieved, the process 600 proceeds to block 620, wherein the pump speed resulting from the parameter adjustment and the one or several threshold values are compared. At block 622, it is determined if one or several of the one or several threshold values are exceeded and thus the pump speed resulting from the parameter adjustment would be greater or less than the maximum or minimum allowable pump speeds.

If it is determined that one of the thresholds is exceeded, then the process 600 proceeds to block 624, wherein the parameter adjustment is set as equal to the threshold value and/or to the maximum or minimum allowable pump speed. After setting the parameter adjustment equal to the pump speed and/or if it is determined that the threshold is not exceeded, then the process 600 proceeds to block 626, wherein the blood pump 12 is controlled according to the parameter adjustment. In some embodiments, the blood pump 12 can be controlled via the generating and/or sending of one or several control signals. In some embodiments, these control signals can be generated by the on-board electronics 24 of the pump 12. In some embodiments, for example, the processor 200 of the controller 23 can generate one or several control signals which can be sent to the blood pump 12 via the communications module 202 of the controller 23.

Other variations are within the spirit of the present invention. Thus, while the invention is susceptible to various modifications and alternative constructions, certain illustrated embodiments thereof are shown in the drawings and have been described above in detail. It should be understood, however, that there is no intention to limit the invention to the specific form or forms disclosed, but on the contrary, the intention is to cover all modifications, alternative constructions, and equivalents falling within the spirit and scope of the invention, as defined in the appended claims.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. The term "connected" is to be construed as partly or wholly contained within, attached to, or joined together, even if there is something intervening. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate embodiments of the invention and does not pose a limitation on the scope of the invention unless otherwise claimed. No language in the specification should be construed as indicating any non-claimed element as essential to the practice of the invention.

The preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

All references, including publications, patent applications, and patents, cited herein are hereby incorporated by reference to the same extent as if each reference were individually and specifically indicated to be incorporated by reference and were set forth in its entirety herein.

What is claimed is:

1. A method of controlling a blood pump to increase battery life of an implantable cardiac rhythm management device, the method comprising:
   receiving a signal of an impending electrical treatment at a processor;
   determining a current operating parameter of the blood pump operably and communicatively coupled with the processor;
   in response to receiving the signal, determining an adjustment to the operating parameter of the blood pump to reduce an impedance of a heart to be affected by the impending electrical treatment, wherein the determined adjustment reduces an amount of energy required to deliver the impending electrical treatment; and
   controlling the blood pump for a first period of time based on the determined adjustment to reduce the impedance of the heart to be affected by the impending electrical treatment.

2. The method of claim 1, wherein the signal of the impending electrical treatment is received by a controller of the blood pump.

3. The method of claim 1, wherein the current operating parameter of the blood pump comprises at least one of: a pump speed; or a pumping operation mode, and wherein the pumping operation mode comprises at least one of: continuous pumping; or pulsatile pumping.

4. The method of claim 3, wherein determining the adjustment to the operating parameter of the blood pump comprises determining to at least one of: increase the pump speed; decrease the pump speed; or change the pumping operation mode to one of:
   continuous pumping; or pulsatile pumping.

5. The method of claim 4, wherein the adjustment is determined based on at least one heart property.

6. The method of claim 4, wherein controlling the blood pump based on the determined adjustment to the operating parameter of the blood pump reduces the impedance of the heart to be affected by the impending electrical treatment.

7. The method of claim 6, wherein the blood pump is controlled based on the determined adjustment to the operating parameter of the blood pump until a desired impedance range is determined.

8. The method of claim 6, further comprising: determining delivery of the electrical treatment; and reverting to the current operating parameter subsequent to determining delivery of the electrical treatment.

9. The method of claim 8, wherein determining delivery of the electrical treatment comprises at least one of: receiving a signal of completion of electrical treatment; or detecting delivery of the electrical treatment.

10. The method of claim 9, wherein detecting delivery of the electrical treatment comprises at least one of: sensing an electrical attribute indicative of delivery of the electrical treatment; or sensing a vibration or conduction indicative of delivery of the electrical treatment.

11. The method of claim 8, further comprising waiting a predetermined time after receipt of the signal of the impending electrical treatment before reverting to the current operating parameter.

12. The method of claim 1, wherein the signal of an impending electrical treatment is received at the processor from the cardiac rhythm management device configured to: determine to deliver the electrical treatment; transmit the signal of the impending electrical treatment; wait a predetermined time after transmitting the signal of the impending electrical treatment; and deliver the electrical treatment subsequent to waiting the predetermined time.

13. The method of claim 12, wherein the impending electrical treatment is delivered after the impedance of the heart is affected according to the determined adjustment, based on an output signal transmitted from the heart pump, or after a second period of time.

14. The method of claim 12, further comprising receiving at least one of: an additional signal of an additional impending electrical treatment when the delivered electrical treatment is determined as ineffective; and a signal of completion of electrical treatment when the delivered electrical treatment is determined as effective.

15. The method of claim 1, wherein the electrical treatment comprises at least one of: electroshock defibrillation; or electrical impulses.

16. The method of claim 1, wherein the signal of the impending electrical treatment is received via at least one of: a wireless communication; and a wire coupled to the cardiac rhythm management device and to at least one of: the blood pump and the processor.

17. The method of claim 16, wherein the signal of the impending electrical treatment is wirelessly received via a wireless receiver.

18. The method of claim 1, wherein the cardiac rhythm management device comprises at least one of: a cardioverter defibrillator, a cardiac resynchronization therapy device, or a pacemaker, and wherein the blood pump comprises a ventricular assist device.

19. A heart blood pump controller comprising:
   a communication module configured to transmit and receive data from a cardiac rhythm management device;
   memory comprising stored instructions; and
   a processor configured to:
   receive a signal of an impending electrical treatment;
   determine a current operating parameter of a heart blood pump operably and communicatively coupled with the processor;
   determine an adjustment to the operating parameter of the blood pump to reduce an impedance of a heart to be affected by the impending electrical treatment, wherein the determined adjustment reduces an amount of energy required to deliver the impending electrical treatment; and
   control the blood pump according to the adjustment to the operating parameter of the blood pump.

20. The heart blood pump controller of claim 19, wherein the signal of the impending electrical treatment is received from the cardiac rhythm management device communicatively coupled with the heart blood pump controller.

21. The heart blood pump controller of claim 19, wherein the current operating parameter of the blood pump comprises at least one of: a pump speed; or a pumping operation mode, and wherein determining the adjustment to the operating parameter of the blood pump comprises determining to at least one of: an increase of the pump speed; a decrease the pump speed; or a change in the pumping operation mode.

22. The heart blood controller of claim 21, wherein the pumping operation mode comprises at least one of: continuous pumping; or pulsatile pumping.

23. The heart blood pump controller of claim 21, wherein the processor is further configured to:
   determine delivery of the electrical treatment, wherein determining delivery of the electrical treatment comprises at least one of: receiving a signal of completion of the electrical treatment; detecting delivery of the electrical treatment; and waiting a first predetermined time after receipt of the signal of the impending electrical treatment; and
   revert to the current operating parameter.

24. The heart blood pump controller of claim 23, wherein detecting delivery of the electrical treatment comprises at least one of: sensing an electrical attribute indicative of delivery of the electrical treatment; and sensing a vibration indicative of delivery of the electrical treatment.

25. The heart blood pump controller of claim 19, wherein the blood pump is controlled for a first period of time based on the determined adjustment to reduce the impedance of the heart to be affected by the impending electrical treatment.

26. The heart blood pump controller of claim 19, wherein the processor is configured to adjust the operating parameter of the blood pump until a desired impedance is determined.

27. The heart blood pump controller of claim 19, wherein the controller is at least one of: an external controller; or an implantable controller.

28. The heart blood pump controller of claim 27, wherein the implantable controller is integral with the blood pump.

29. The heart blood pump controller of claim 27, wherein the implantable controller is separate from the blood pump.

30. The method of claim 4, wherein controlling the blood pump for the first period of time comprises reducing the blood pump speed, wherein reducing the pump speed reduces an output volume of the blood pump.

\* \* \* \* \*